(12) United States Patent
Murase et al.

(10) Patent No.: US 10,125,370 B2
(45) Date of Patent: Nov. 13, 2018

(54) METHOD FOR PRODUCING PROTEIN IN PLANTS USING LIGHTING WITH AT LEAST 50% RED LIGHT

(71) Applicant: MITSUBISHI CHEMICAL CORPORATION, Chiyoda-ku (JP)

(72) Inventors: Makoto Murase, Yokohama (JP); Daisuke Kitahara, Yokohama (JP); Nobuhiro Ikezawa, Yokohama (JP); Hiroyuki Tanaka, Yokohama (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 15/061,466

(22) Filed: Mar. 4, 2016

(65) Prior Publication Data

US 2016/0281098 A1 Sep. 29, 2016

Related U.S. Application Data

(63) Continuation of application No. PCT/JP2014/073474, filed on Sep. 5, 2014.

(30) Foreign Application Priority Data

Sep. 6, 2013 (JP) ................................ 2013-184923

(51) Int. Cl.
| | |
|---|---|
| C12N 15/82 | (2006.01) |
| C12N 15/67 | (2006.01) |
| C12N 7/00 | (2006.01) |
| C12N 9/24 | (2006.01) |

(52) U.S. Cl.
CPC ........... *C12N 15/8205* (2013.01); *C12N 7/00* (2013.01); *C12N 9/2402* (2013.01); *C12N 15/67* (2013.01); *C12N 15/8257* (2013.01); *C12Y 302/01045* (2013.01); *C12N 2770/16023* (2013.01); *C12N 2770/16051* (2013.01)

(58) Field of Classification Search
None
See application file for complete search history.

(56) References Cited

U.S. PATENT DOCUMENTS

| 4,817,332 | A | * | 4/1989 | Ikeda ....................... A01G 7/02 |
| | | | | 47/17 |
| 6,921,182 | B2 | * | 7/2005 | Anderson, Jr. ......... A01G 7/045 |
| | | | | 362/230 |
| 2005/0022267 | A1 | | 1/2005 | Ryu et al. |
| 2008/0057563 | A1 | | 3/2008 | Marillonnet et al. |
| 2010/0239610 | A1 | | 9/2010 | D'Aoust et al. |
| 2012/0178149 | A1 | | 7/2012 | Vezina et al. |
| 2013/0212739 | A1 | | 8/2013 | Giritch et al. |

FOREIGN PATENT DOCUMENTS

| JP | 5-41990 | 2/1993 |
| JP | 9-37648 | 2/1997 |
| JP | 2001-54320 | 2/2001 |
| JP | 2008-505622 | 2/2008 |
| JP | 2009-528025 | 8/2009 |
| JP | 2010-533001 | 10/2010 |
| JP | 2011-55834 | 3/2011 |
| JP | 2013-505025 | 2/2013 |
| JP | 2013-532992 | 8/2013 |
| WO | WO 2007/095304 A2 | 8/2007 |
| WO | WO 2012/007587 A1 | 1/2012 |

OTHER PUBLICATIONS

Santi et al. An efficient plant viral expression system generating orally immunogenic Norwalk virus-like particles. (2008) Vaccine; vol. 26; pp. 1846-1854.*
Benfey et al. The Cauliflower Mosaic Virus 35S Promoter: Combinatorial Regulation of Transcription in Plants. (1990) Science; vol. 250; pp. 959-966.*
Halliday et al. Phytochrome B and at Least One Other Phytochrome Mediate the Accelerated Flowering Response of *Arabidopsis thaliana* L. to Low Red/Far-Red Ratio. (1994) Plant Physiology; vol. 104; pp. 1311-1315.*
International Search Report dated Dec. 8, 2014 in PCT/JP2014/073474 filed on Sep. 5, 2014.
Eiji Goto, "Application of LEDs to Plant Production", Journal of the Illuminating Engineering Institute of Japan, vol. 89, (3), 2005, 5 pgs.
Ryo Matsuda, et al., "Virus Vector-Mediated Rapid Protein Production in Nicotiana benthamiana: Effects of Temperature and Photosynthetic Photon Flux Density on Hemagglutinin Accumulation", Environ. Control Biol., vol. 50, (4), 2012, 7 pgs.
Office Action as received in the corresponding Japanese Patent Application No. 2015-535526 dated Dec. 26, 2017 w/English Translation.

* cited by examiner

*Primary Examiner* — Cathy Kingdon Worley
(74) *Attorney, Agent, or Firm* — Oblon, McClelland, Maier & Neustadt, L.L.P.

(57) ABSTRACT

A method for producing a useful protein using a plant of the present invention comprises the steps of:
  cultivating the plant (cultivation step);
  infecting the cultivated plant with *Agrobacterium* having a polynucleotide encoding the useful protein (infection step); and
  allowing the infected plant to express the useful protein (expression step); wherein, in at least part of the cultivation step, the plant is cultivated under lighting conditions where the ratio of the light energy within the wavelength region of 600 nm to 700 nm to the light energy within the wavelength region of 400 nm to 800 nm is not less than 50%.

19 Claims, 6 Drawing Sheets

[Fig.1]

35S$^P$: Cauliflower mosaic virus 35S promoter
int: Castor bean catalase gene first intron
Nos$^t$: Nopaline synthase terminator
Spec$^R$: Spectinomycin resistance gene
Tc$^R$: Tetracycline resistance gene
Hm$^R$ : Hygromycin resistance gene
Ori$^{pBR322}$: pBR322 ori
Ori$^{pRK2}$: pRK2 ori
B$^L$: T-DNA left border
B$^R$: T-DNA right border

[Fig.2]

35S^P: Cauliflower mosaic virus 35S promoter
int: Castor bean catalase gene first intron
Nos^t: Nopaline synthase terminator
Spec^R: Spectinomycin resistance gene
Tc^R: Tetracycline resistance gene
Ori^pBR322: pBR322 ori
Ori^pRK2: pRK2 ori
B^L: T-DNA left border
B^R: T-DNA right border

[Fig.3]

[Fig.5]
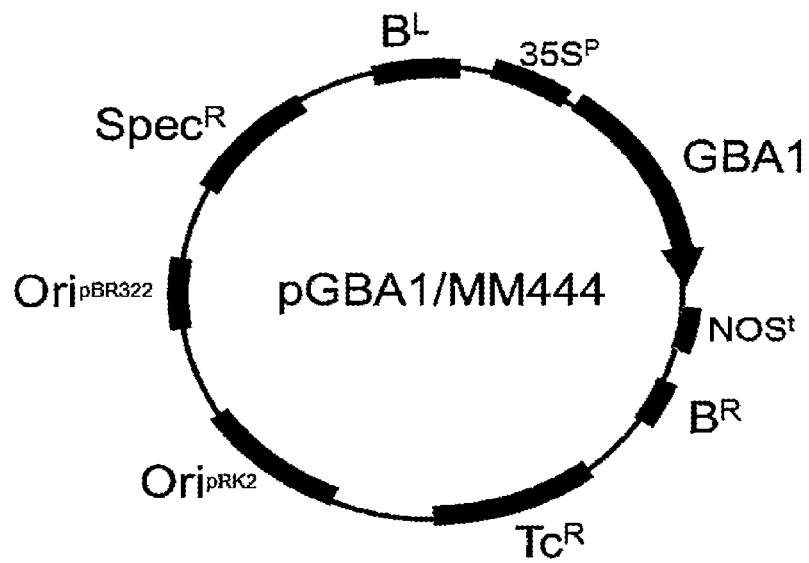
35S$^P$: Cauliflower mosaic virus 35S promoter
Nos$^t$: Nopaline synthase terminator
Spec$^R$: Spectinomycin resistance gene
Tc$^R$: Tetracycline resistance gene
Ori$^{pBR322}$: pBR322 ori
Ori$^{pRK2}$: pRK2 ori
B$^L$: T-DNA left border
B$^R$: T-DNA right border

[Fig.6]
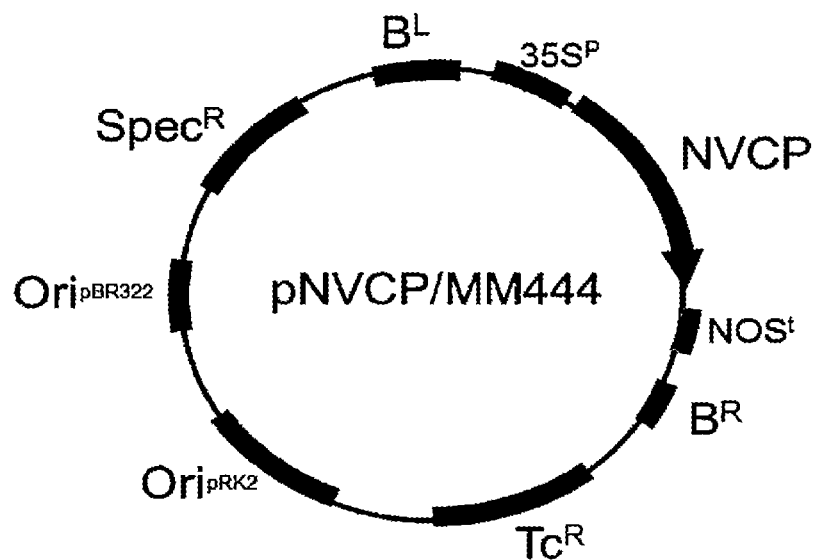
35S$^P$: Cauliflower mosaic virus 35S promoter
Nos$^t$: Nopaline synthase terminator
Spec$^R$: Spectinomycin resistance gene
Tc$^R$: Tetracycline resistance gene
Ori$^{pBR322}$: pBR322 ori
Ori$^{pRK2}$: pRK2 ori
B$^L$: T-DNA left border
B$^R$: T-DNA right border

METHOD FOR PRODUCING PROTEIN IN PLANTS USING LIGHTING WITH AT LEAST 50% RED LIGHT

TECHNICAL FIELD

The present invention relates to a method for efficiently producing a useful protein using a plant.

BACKGROUND ART

In recent years, methods for producing a protein using a plant are drawing attention since, for example, in such methods, expression of a complex protein is possible; mass production of a protein is possible at low cost; separation/purification of a protein can be easily carried out; and the safety is assured. Known examples of methods for producing a protein using a plant include those described in the following literatures.

Patent Document 1 describes a method wherein *Nicotiana benthamiana* infected with transformed *Agrobacterium* is cultivated in a greenhouse to produce influenza virus-like particles (VLPs) such as H1 protein.

Patent Document 2 discloses a method wherein a plant is infected with transformed *Agrobacterium* under a specific pressure condition to produce a peptide or protein, and Example 3 describes that the plant to be used for infection was cultivated using, in addition to natural light, artificial light for supplemental lighting.

Non-patent Document 1 describes a method wherein *Nicotiana benthamiana* cultivated with light of a white fluorescent lamp is infected with transformed *Agrobacterium* to allow expression of an antigenic protein for an influenza vaccine, hemagglutinin.

Patent Document 3 describes a method wherein a leaf vegetable is cultivated using only red light having a peak wavelength of 600 to 700 nm.

PRIOR ART DOCUMENTS

Patent Documents

[Patent Document 1] Japanese Translated PCT Patent Application Laid-open No. 2010-533001
[Patent Document 2] WO2012/007587
[Patent Document 3] JP 9-37648 A

Non-Patent Documents

[Non-patent Document 1] Environ. Control. Biol., 2012, 50 (4), 375-381

SUMMARY OF INVENTION

Problems to be Solved by the Invention

Although, as described above, techniques for producing a protein using a plant have been known, conditions for improving the production efficiency in these techniques have not been sufficiently studied.

That is, in Patent Document 1, there is no description on the type of the light source in the cultivation step for the plant, and there is no specific description on the wavelength of the light source. Further, the light source in the step of cultivating the plant has not been studied.

Although Patent Document 2 describes expression of a protein using a plant cultivated under conditions where natural light as well as artificial light are used, there is no description on the wavelength of the artificial light at all, and the wavelength of the light source in the step of cultivating the plant has not been studied.

In Non-patent Document 1, conditions for expression of a protein in a plant infected with *Agrobacterium* have been studied for improvement of the expression level of the protein, but the plant used in the cultivation step was cultivated using a white fluorescent lamp, and a preferred light source has not been studied.

Further, the object of Patent Document 3 is cultivation of a plant, and it does not describe production of a protein using a plant at all.

As described above, in transient expression of a protein in a plant, natural light and/or a white fluorescent lamp is/are used as the light source in the cultivation step, and there has been no report in which a light source emitting light within the wavelength region of 600 nm to 700 nm (red light) at more than a certain ratio was used for the cultivation.

Thus, the present invention aims to improve conditions for cultivation of a plant in production of a useful protein using the plant, in order to increase the efficiency of production of the useful protein.

Means for Solving the Problems

The present inventors intensively studied for solving the above problems. As a result, the present inventors discovered that, by using a plant cultivated under conditions where light within the wavelength region of 600 nm to 700 nm ("so-called red light", which may be simply referred to as "red light") is present at more than a certain ratio for transient expression of a protein, the expression efficiency and the expression level of the protein can be increased, thereby completing the present invention.

That is, the present invention can be summarized as follows.

[1] A method for producing a useful protein using a plant, the method comprising the steps of:
cultivating the plant (cultivation step);
infecting the cultivated plant with *Agrobacterium* having a polynucleotide encoding the useful protein (infection step); and
allowing the infected plant to express the useful protein (expression step);
wherein, in at least part of the cultivation step, the plant is cultivated under lighting conditions where the ratio of the light energy within the wavelength region of 600 nm to 700 nm to the light energy within the wavelength region of 400 nm to 800 nm is not less than 50%.

[2] The method for producing a useful protein according to [1], wherein the cultivation of the plant in at least part of the cultivation step is carried out under lighting conditions where the ratio of the light energy within the wavelength region of 600 nm to 700 nm to the light energy within the wavelength region of 400 nm to 800 nm is not less than 75%.

[3] The method for producing a useful protein according to [1] or [2], further comprising the step of purifying and collecting the useful protein after the expression step.

[4] The method for producing a useful protein according to any one of [1] to [3], wherein the useful protein is a pharmaceutical protein.

[5] The method for producing a useful protein according to any one of [1] to [4], wherein the plant is *Nicotiana benthamiana*.

[6] The method for producing a useful protein according to any one of [1] to [5], wherein the plant is cultivated in a closed plant factory in the cultivation step.

[7] The method for producing a useful protein according to any one of [1] to [6], wherein an LED is used as a light energy source in the cultivation step.

[8] An enzyme or virus-like particles produced by the method according to any one [1] to [7].

Effect of the Invention

According to the method of the present invention, a plant cultivated under conditions where light within the wavelength region of 600 nm to 700 nm (red light) is present at more than a certain ratio has an increased expression efficiency of protein, so that a protein can be efficiently produced with the plant. Further, unlike conventional techniques wherein the amount of growth is increased by controlling the light condition, the present invention allows accumulation of a protein in a plant at high concentration, so that the purification load can be reduced in the step of purification of a protein, and the production cost can therefore be effectively reduced.

BRIEF DESCRIPTION OF THE DRAWINGS

FIG. 5 illustrates the structure of the plasmid pGBA1/MM444.

FIG. 6 illustrates the structure of the plasmid pNVCP/MM444.

EMBODIMENTS FOR CARRYING OUT THE INVENTION

Figure 1:
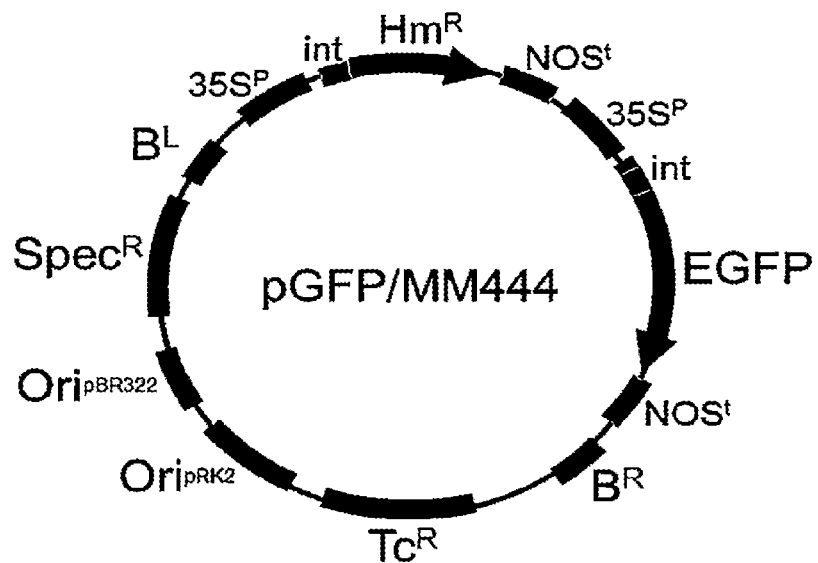
FIG. 1 illustrates the structure of the plasmid pGFP/MM444.
Figure 2:
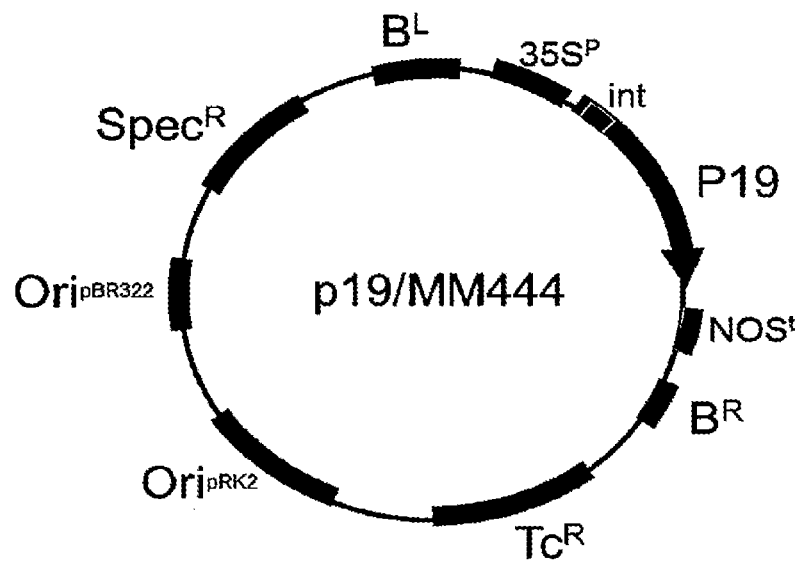
FIG. 2 illustrates the structure of the plasmid p19/MM444.

Embodiments of the present invention are described below in detail.

The method of the present invention for producing a useful protein using a plant comprises the steps of: cultivating the plant (cultivation step); infecting the cultivated plant with *Agrobacterium* having a polynucleotide encoding the useful protein (infection step); and cultivating the infected plant to allow expression of the useful protein (expression step).

The plant that may be used in the present invention is not limited as long as the plant can be infected with *Agrobacterium* and can express a useful protein. Examples of the plant include dicotyledons and monocotyledons. Examples of the dicotyledons include solanaceous plants including tobacco, potato and tomato; cruciferous plants including arugula, Japanese mustard spinach, potherb mustard, Indian mustard and *Arabidopsis thaliana*; asteraceous plants including chicory, endive and artichoke; leguminous plants including alfalfa, mung bean and soybean; chenopodiaceous plants including spinach and sugar beet; labiatae plants including perilla and basil; and apiaceous plants including Japanese honewort. Examples of the monocotyledons include graminaceous plants including rice, wheat, barley and maize; and malvaceous plants including cotton. Among these, solanaceous plants are preferred, and tobacco is more preferred.

Examples of the tobacco include *Nicotiana tabacum*, *N. benthamiana*, *N. alata*, *N. glauca*, *N. longiflora*, *N. persica*, *N. rustica* and *N. sylvestris*. *N. benthamiana* is preferred.

In the present invention, the useful protein is not limited as long as it is a protein used for a medical or industrial purpose. A protein used for a medical purpose is preferred.

Examples of the pharmaceutical protein include peptides, vaccines, antibodies, enzymes and hormones (preferably peptide hormones). More specific examples of the pharmaceutical protein include: viral proteins to be used as vaccines; granulocyte colony-stimulating factor (G-CSF); granulocyte-macrophage colony-stimulating factor (GM-CSF); hematopoietic factors such as erythropoietin (EPO) and thrombopoietin; cytokines such as interferons and interleukins (IL)-1 and IL-6; monoclonal antibodies and fragments thereof; tissue plasminogen activators (TPAs); urokinase; serum albumin; blood coagulation factor VIII; leptin; insulin; and stem cell factor (SCF).

Preferred examples of the viral proteins to be used as vaccines include the constituent protein of virus-like particles (VLPs). The constituent protein of VLPs may be a single protein, or may comprise two or more proteins. Examples of the virus include influenza virus, norovirus, human immunodeficiency virus (HIV), human hepatitis C virus (HCV) and human hepatitis B virus (HBV). Examples of a constituent protein of the VLP of influenza virus include influenza hemagglutinin (HA) protein. Examples of a constituent protein of the VLP of norovirus include Norwalk virus capsid protein (NVCP).

The protein for an industrial purpose means a protein used as a food, feed, cosmetic, fiber, detergent or chemical product, and examples of the protein for an industrial purpose include peptides, enzymes and functional proteins. Specific examples of the protein for an industrial purpose include protease, lipase, cellulase, amylase, peptidase, luciferase, lactamase, collagen, gelatin, lactoferrin and jellyfish green fluorescent protein (GFP).

Each step of the production method of the present invention is described below.

<Cultivation Step>

As described later, at least part of the present invention comprises the step of cultivating the plant under lighting conditions where the ratio of the light energy (spectral irradiance, W/m$^2$/nm) within the wavelength region of 600 nm to 700 nm to the light energy within the wavelength region of 400 nm to 800 nm is not less than 50%.

In the cultivation step, any plant-based production system may be used as long as the cultivation can be carried out under the above-described conditions. In view of simplicity of controlling the light energy during the cultivation, a semiclosed or closed plant factory is preferred, and a closed plant factory is more preferred. Examples of the semiclosed type include horticultural facilities and solar plant factories.

The closed plant factory herein means a plant factory operated in the absence of sunlight, and is a system for cultivating a plant in a space where, for example, the temperature, humidity, carbon dioxide concentration, and the wavelength and the irradiation time of artificial light are controlled. Use of a closed plant factory has an effect to stabilize the qualities of the plant and the substance produced thereby since the light can controlled, and also has an effect to prevent infection with pathogens contained in the outdoor air. It is preferable because it enables fine control of environmental conditions for cultivation such as temperature, moisture, air flow and others and because it has an effect to increase growth rate of the plant in the cultivation step as well as the expression of the useful protein in the expression step.

Examples of the closed plant factory include a system comprising: an environment-controlled room; a plant cultivation container shelf placed in the environment-controlled room, which shelf is used for mounting plant cultivation containers thereon; and an illuminator that is placed in the vicinity of the plant cultivation container shelf and used for short distance irradiation of light to the plant. The plant cultivation container shelf may be in the form of a multi-level shelf.

The height (cm) of the plant cultivated in the cultivation step is preferably not less than 2 cm, more preferably not less than 3 cm, but preferably not more than 25 cm, more preferably not more than 15 cm. In cases where the height is within this range, the STY (space time yield) of the closed plant factory can be advantageously increased by use of a multi-level cultivation shelf.

When a plant is used which can accumulate a high concentration of protein in the plant, ratio of leaves in the aerial part is increased as the height of the plant is less than an upper limit. It increases the yield of leaves per plant and it is possible to ensure sufficient amount of protein. Leaves are easy to handle. It is preferable that an increase of the weight ratio of leaves enables to reduce the purification load, and as a result, to readily ensure the protein.

Here, "height of the plant" means the length from the lower end to the shoot apex of the aerial part, and it can be calculated by measuring the length of the height of the plant after cutting off the ground part of a plant just after harvest.

The aerial part fresh weight (g) of the plant cultivated in the cultivation step is preferably not less than 3 g, more preferably not less than 10 g, but preferably not more than 100 g, more preferably not more than 70 g. In cases where the aerial part fresh weight is within this range, the plant shows a high growth rate, and use of the plant during a period with such a high growth rate allows improvement of the production efficiency of the useful protein, which is preferred.

The leaf weight (g) of the plant cultivated in the cultivation step is preferably not less than 2.5 g, more preferably not less than 7.5 g, but preferably not more than 80 g, more preferably not more than 60 g. In cases where the leaf weight is within this range, the plant shows a high growth rate, and use of the plant during a period with such a high growth rate allows improvement of the production efficiency of the useful protein, which is preferred.

The cultivation conditions are not limited as long as the conditions are appropriate for the growth of the plant and production of the useful protein, and, for example, the plant may be cultivated under the conditions described below.

The temperature in the plant factory is usually not less than 10° C., preferably not less than 15° C., but usually not more than 40° C., preferably not more than 37° C.

The humidity in the plant factory is usually not less than 40%, preferably not less than 50%, but usually not more than 100%, preferably not more than 95%.

The carbon dioxide concentration in the plant factory is usually not less than 300 ppm, preferably not less than 500 ppm, but usually not more than 5000 ppm, preferably not more than 3000 ppm.

The light source used in the cultivation step is not limited as long as the above-described light energy condition can be satisfied, and examples of the light source include sunlight, fluorescent lamps, LEDs, cold cathode fluorescent lamps (CCFLs, HEFLs) and inorganic/organic ELs. The light source is preferably a fluorescent lamp, LED or cold cathode fluorescent lamp, more preferably an LED. An LED is preferred since it has higher light conversion efficiency and consumes less power as compared to an incandescent lamp or HID lamp. Further, an LED is preferred also in view of the fact that it emits only a low level of heat rays that cause leaf burn in the plant.

The light was classified based on the wavelength into: blue light (B), which has a wavelength of 400 to 500 nm; green light (G), which has a wavelength of 501 to 600 nm; red light (R), which has a wavelength of 601 to 700 nm; and far infrared (FR), which has a wavelength of 701 to 800 nm.

The wavelength ranges are used for the sake of convenience when the wavelength of a visible light is classified by the color of the light in order to carry out an operation in a wavelength range whose boundary to the adjacent wavelength range is not overlapped. When a wavelength range including a red light is simply described as 600 to 700 nm, it means that the wavelength range may include the wavelengths of both ends.

In the cultivation step, the plant is cultivated under light conditions in which the ratio of the light energy (spectral irradiance; $W/m^2/nm$) within the wavelength region of 600 nm to 700 nm to the light energy within the wavelength region of 400 nm to 800 nm is usually not less than 50%, preferably not less than 75%, more preferably not less than 90%. The light energy can be measured using a spectroradiometer (Specbos 1211, manufactured by Five Lab) or the like. In cases where a plant cultivated within this wavelength range is used in the infection step, the protein expression efficiency of the plant is high, and therefore the protein yield is high, which is preferred.

In the cultivation step, reduction of the ratio of far-infrared light of 700 to 800 nm in the irradiated light cause a preferable result of shorter height of the obtained plants. Specifically, the plants are cultivated under the light source with the ratio (FR/R) of light energy (spectral irradiance, $W/m^2/nm$) of far-infra red light (FR, wavelength 701 to 800 nm) to red light (R, wavelength 601 to 700 nm) of not more than 0.25 preferably, not more than 0.2 more preferably, and not more than 0.15 further preferably. The plant may be cultivated under the light source which is not comprised of far-infra red light (FR, wavelength 701 to 800 nm).

When a plant is used which can accumulate high concentration of protein, it is possible to ensure sufficient amount of protein by setting the above-mentioned FR/R value not more than 0.25, resulting in higher ratio of the leaves in the entire aerial part and higher yield of leaves per plant. It is preferable that the increased weight ratio of leaves, which is easy to handle in the purification step, enables to reduce the purification load, and as a result, to readily ensure the protein. It is also preferable that a multi-level cultivation is advantageous to the STY of the plant factory.

There is no need to keep the light energy condition as mentioned in the above throughout the entire course of cultivation step. The plants may be cultivated under the above-mentioned conditions only a certain period of the cultivation step; for example, the plants may be cultivated under the above-mentioned light energy condition only during the second half of the cultivation step. In such a case, the period in which the plants are cultivated under the above-mentioned conditions is preferably no less than 1%, and more preferably no less than 20% of the entire time of cultivation step.

During the course of the cultivation step when the plants are not cultivated under the above-mentioned light energy condition, the plants may be cultivated under any light energy condition, and the plants may be cultivated in the open plant factory under the sunlight.

It is presumed that the plants obtained by cultivation under the above-mentioned conditions have reduced defense against agrobacteria infection and increased infection efficiency as compared to the ordinary plants. It is possible that the expression efficiency of the protein of interest in the transient expression is increased as a consequence. In case of tobacco plants, examples of possible factors responsible for the decrease in the protective capacity include, for example, reduction of nicotine content in the plant and reduction of polysaccharide constituents of cell wall. Nicotine is an alkaloid playing a role in protecting the plant body from the outside. The cell wall has a barrier function to the outside. It is assumed that the red light irradiation decreases the nicotine metabolic rate in the plant and the amount of production of polysaccharides contained in the cell wall, resulting in the increased susceptibility to infection with *Agrobacterium*. Further, it is considered that, by cultivating the plant under the above-described condition, production of specific proteins contained in the plant is suppressed, and the expression efficiency of the protein of interest increases as a result. Examples of the specific proteins include protease. Suppression of production of protease leads to suppression of degradation of the protein of interest, which then results in an increased expression efficiency of the protein.

Accordingly, the plants obtained in the cultivation step of the present invention can be efficiently infected with *Agrobacterium* a polynucleotide introduced in the infection step with *Agrobacterium* can express a protein at a high efficiency. As a result, it is considered to increase efficiency and level of expressed protein of interest. This effect is expected regardless of the identity of the protein of interest.

Further, in the cultivation step, the plant is preferably cultivated in a cycle in which light is irradiated for not less than 10 hours but less than 24 hours per day, or in continuous light. In particular, the cultivation is more preferably carried out in continuous light. Within the above-described range, the growth rate of the plant is high, and the cultivation period required before harvesting can be short, which is preferred. The term "light is irradiated for not less than 10 hours but less than 24 hours per day" does not necessarily mean continuous irradiation, and, for example, in cases where the irradiation time is 20 hours per day, not less than 10 hours of continuous irradiation may be carried out twice a day.

The light irradiated in the step may be pulsed light. The pulsed light is obtained by turning an LED or the like on and off at intervals of as short as 1 microsecond to 1 second. By using such pulsed light, irradiation of light to the plant can be omitted when the plant does not physiologically need light, and light can be irradiated to the plant only when the plant needs light. This can increase the photosynthetic rate, while the electricity cost can be reduced. The irradiation time in such a case also includes the time during which the LED is turned off, and is the total time per day during which the pulsed light is irradiated.

The method for cultivating a plant in the cultivation step is not limited as long as the method is suitable for the growth of the plant and production of the useful protein. The plant is preferably cultivated using a hydroponic system. Preferred examples of the hydroponic system include those using no natural solid medium (soil), and, more specifically, cultivation using an artificial solid medium, hydroponics, or cultivation by spraying is preferred. Among these, hydroponics is more preferred since this easily allows use of a multi-level cultivation shelf, recycling of the nutrient solution, and control of fertilizer components and the pH. Examples of the hydroponics include NFT (Nutrient Film Technique) and DFT (Deep Flow Technique). Among the hydroponic systems, the bare-root method, in which bare roots are immersed in a nutrient solution, is especially preferred. This is because the roots freely extend in water and the area of contact with the nutrient solution therefore increases. This allows absorption of sufficient amounts of water and nutrients, leading to faster growth of the plant than in soil cultivation.

The number of days of cultivation in the cultivation step is usually not less than 5 days, preferably not less than 7 days, more preferably not less than 10 days, but usually not more than 35 days, preferably not more than 28 days, more preferably not more than 21 days.

In the cultivation step, transplantation may be carried out as required. The timing of transplantation is preferably 6 days to 15 days after the start of cultivation.

In the production method of the present invention, a step of raising a seedling is preferably carried out before the cultivation step. The step of raising a seedling means a step that allows sprouting and growth of a seedling of the plant for a predetermined period under an artificial environment, until transplantation of the plant for the cultivation step. The conditions such as the temperature and the humidity for the step of raising a seedling may be the same as the conditions for the cultivation step. The condition of light irradiation may also be a usual condition that can be achieved using sunlight, a fluorescent lamp, an LED, a cold cathode fluorescent lamp (CCFL, HEFL), an inorganic/organic EL or the like. In the step of raising a seedling, the seedling of the plant is preferably grown in a cycle in which light is irradiated for 12 hours to 24 hours per day. The term "light is irradiated for 12 hours to 24 hours per day" does not necessarily mean continuous irradiation, and, for example, in cases where the irradiation time is 20 hours per day, not less than 10 hours of continuous irradiation may be carried out twice a day.

<Infection Step>

In the infection step, the plant obtained by the cultivation step is infected with *Agrobacterium* having a polynucleotide encoding a useful protein.

The polynucleotide encoding a useful protein means a polynucleotide encoding the useful protein of interest. The useful protein of interest means a protein exemplified above as a useful protein. The polynucleotide may have a wild-type sequence, or may be mutated or modified as appropriate such that the useful protein of interest can be obtained.

For overexpression of the polynucleotide encoding a useful protein in a plant, the polynucleotide may be functionally linked downstream of an appropriate promoter, and the obtained polynucleotide construct may be introduced into plant cells by the *Agrobacterium* method. Examples of the promoter include, but are not limited to, the 35S promoter of cauliflower mosaic virus (CaMV), the actin promoter and the Elongation factor 1β promoter of rice, and the ubiquitin promoter of maize.

When the *Agrobacterium* method is carried out, a binary vector or an inteunediate vector comprising T-DNA (transfer DNA) derived from Ti plasmid or Ri plasmid of *Agrobac-* terium may be used (Nucl. Acids Res. 12 (22): 8711-8721 (1984); Plasmid, 7, 15-29 (1982)). Specific examples of the binary vector include, but are not limited to, pBI vectors (e.g., pRiceFOX), pPZP vectors (Plant Molecular Biology 25 (6): 989-94. (1994)), pCAMBIA vectors (vector skeleton: pPZP vector) and pSMA vectors (Plant Cell Reports 19: 448-453. (2000)).

For expression of the polynucleotide construct, transient expression may be carried out using these vectors (Journal of Virological Methods, 105:343-348 (2002)). The infection with *Agrobacterium* is preferably carried out under reduced pressure, and the transient expression method described in Plant Science, 122, 1: 101-108 (1997), which is carried out under vacuum, is preferably used. By agroinoculation or agroinfiltration, *Agrobacterium* comprising the polynucleotide construct enters into the space between cells in a tissue such as leaf, a part of the aerial portion of the plant (including stems, leaves and flowers), a part of other portions of the plant (stems, roots and flowers), or the whole plant. Infection with *Agrobacterium* occurs after its passing through the epidermis, and the polynucleotide is transferred into the cell. The polynucleotide as an episome is transcribed, and the resulting mRNA is translated to produce the protein of interest in the infected cell. The polynucleotide is only transiently present in the nucleus.

<Expression Step>

In the expression step, the infected plant is cultivated for expression of the useful protein. The cultivation conditions in the expression step are not limited as long as the useful protein can be efficiently expressed, and conditions such as the temperature and the humidity for the expression step may be the same as those for the cultivation step. The condition of light irradiation may also be a usual condition that can be achieved using sunlight, a fluorescent lamp, an LED, a cold cathode fluorescent lamp (CCFL, HEFL), an inorganic/organic EL or the like. In the expression step, the number of days of cultivation is preferably not less than 3 days, more preferably not less than 4 days, but preferably not more than 14 days, more preferably not more than 10 days.

<Step of Recovery of Useful Protein>

Preferably, in the expression step, the useful protein accumulated in the plant body is collected from the plant. Preferably, a fraction comprising the useful protein is obtained from the plant, and the useful protein is purified by an appropriate method. The polynucleotide encoding the useful protein may comprise a tag sequence for purification.

EXAMPLES

The present invention is described below in more detail by way of Examples, but the present invention is not limited by these Examples at all.

Example 1

1. Preparation of Transformed *Agrobacterium*
1.1 Expression Plasmid

For studying expression of GFP (jellyfish green fluorescent protein), the following two kinds of expression plasmids were used.

The kanamycin resistance expression cassette (consisting of the promoters for nopaline synthase gene and kanamycin resistance gene and the terminator of nopaline synthase gene) in the plant binary vector pMM444 (JP 9-313059 A) was replaced with a hygromycin resistance expression cassette (comprising of 35S promoter of cauliflower mosaic virus, the first intron of the catalase gene of castor bean, and the terminator of the nopaline synthase gene) derived from pTZI (JP 7-274752). The obtained plasmid was further engineered to include an EGFP expression cassette prepared by incorporating an EGFP gene (pEGFP-N3, manufactured by CLONTECH) in place of the glucuronidase gene of a GUS expression cassette comprising the 35S promoter of cauliflower mosaic virus, the first intron of the catalase gene of castor bean, a beta-glucuronidase gene and the terminator of the nopaline synthase gene (pIG221: Plant Cell Physiol., p19/MM444 31, 805 (1990)), to prepare an EGFP gene expression plasmid (this plasmid is hereinafter referred to as "pGFP/MM444" (see FIG. 1 for its structure)).

In FIGS. 1, 2, 5 and 6, genes and their control regions are abbreviated as follows:
35SP: 35S promoter of cauliflower mosaic virus;
int: first intron of catalase gene of castor bean;
Nost: terminator of the nopaline synthase gene;
SpecR: spectinomycin resistance gene;
TcR: tetracycline resistance gene;
HmR: hygromycin resistance gene;
OripBR322: pBR322 ori;
BL: T-DNA left border; and
BR: T-DNA right border The hygromycin resistance expression cassette was removed from pGFP/MM444, and the EGFP gene of the EGFP expression cassette was replaced with p19 gene derived from tomato bushy stunt virus to prepare a p19 gene expression plasmid (hereinafter referred to as "p19/MM444" (see FIG. 2 for its structure)). The p19 gene has a function to enhance expression of the EGFP gene, and the plasmid p19/MM444 was subjected to coexpression with pGFP/MM444.

1.2 Transformation of *Agrobacterium* and Preparation of Glycerol Stock of Transformed *Agrobacterium*

Each of the above-described plasmids (pGFP/MM444 and p19/MM444) was introduced into an *Agrobacterium* (*Agrobacterium tumefaciens* AGL1: *Rhizobium radiobacter* ATCC BAA-101; American Type Culture Collection (ATCC), Manassas, Va. 20108, USA) strain by electroporation (Mattanovich et al. 1989) (the obtained transformed *Agrobacterium* strains are hereinafter referred to as GFP-*Agrobacterium* and p19-*Agrobacterium*, respectively).

Each of the transformed *Agrobacterium* strains (GFP-*Agrobacterium* and p19-*Agrobacterium*) was cultured in LB medium (manufactured by SIGMA-ALDRICH) supplemented with 25 µg/ml carbenicillin and 50 µg/ml spectinomycin, and glycerol was added to the resulting culture such that the final glycerol concentration was 30%, followed by storing the resulting mixture at −80° C. to prepare a glycerol stock of each transformed *Agrobacterium*.

1.3 Preparation of Transformed *Agrobacterium* for Infection Step

The glycerol stock of each of the transformed *Agrobacterium* strains prepared in Section 1.2 as described above (GFP-*Agrobacterium* and p19-*Agrobacterium*) was inoculated to LB medium, and cultured.

Thereafter, each obtained culture was centrifuged to collect the bacterial cells, and the obtained bacterial cells were suspended in infiltration buffer (5 mM MES, 10 mM $MgCl_2$, pH 5.6), to obtain a concentrated bacterial suspension. The obtained concentrated bacterial suspensions were then added to 4 L of infiltration buffer to prepare a 1:1 bacterial mixture of GFP-*Agrobacterium* and p19-*Agrobacterium* such that OD600 of the mixture was 0.8. The pH of the mixture was then adjusted to 5.6 to provide an *Agrobacterium* suspension for the infection step (for coexpression of GFP and p19).

2. Preparation of Plant Biomass
2.1 Seeding

A urethane mat (Ematsu Kasei; W 587.5 mm×D 282 mm×H 28 mm; 12×2 squares; hole diameter, 9 mm) was impregnated with a liquid fertilizer for seeding (0.78 g/L Otsuka House No. S1 (Otsuka AgriTechno Co., Ltd.) and 0.25 g/L Otsuka House No. 2 (Otsuka AgriTechno Co., Ltd.); pH 5.0), and then placed in a tray for raising seedlings (W 600 mm×D 300 mm×H 300 mm), followed by seeding of *Nicotiana benthamiana* thereon.

2.2 Raising of Seedlings

The plant after seeding was grown in an artificial climate chamber (NC-410HC) (Nippon Medical & Chemical Instruments Co., Ltd.) at a room temperature of 28° C. with a light/dark cycle of 16:8 hours for 12 days.

2.3 Cultivation (Early Period)

Each square of the urethane mat used for raising the seedlings in Section 2.2 was separated, and transplantation to a cultivation (early period) panel (W 600 mm×D 300 mm; 30 holes) was carried out. Thereafter, the cultivation (early period) panel was placed in a cultivation device, and cultivation was carried out for 9 days by the deep flow technique (DFT method). The environmental conditions and the liquid fertilizer conditions were controlled as follows.

<<Environmental Conditions>>

Temperature: 28° C.
Relative humidity: 60 to 80%
$CO_2$ concentration: 400 ppm
Illumination: Average photosynthetic photon flux density (PPFD): 140 µmol/m$^2$/sec.; continuous irradiation for 24 hours; three band fluorescent lamp "Rupika Line" (Mitsubishi Electric Corporation)

<<Liquid Fertilizer Conditions>>

The liquid fertilizer was prepared by dissolving each of the fertilizer A liquid (150 g/L Otsuka House No. S1, 2.5 g/L Otsuka House No. 5 (Otsuka AgriTechno Co., Ltd.)) and the fertilizer B liquid (Otsuka House No. 2, 100 g/L) in dechlorinated water and then mixing equal amounts of the resulting solutions. For pH adjustment, a pH adjuster Down (Otsuka AgriTechno Co., Ltd.) and 4% aqueous KOH solution were used. The electrical conductivity (EC) and the pH of the liquid fertilizer were adjusted to EC: 2.3 mS/cm and pH 6.0, respectively, using "Easy Treatment Fertilizer Controller 3" (CEM Corporation).

2.4 Cultivation (Later Period)

From the cultivation (early period) panel, the plant was removed, and the plant was then transplanted on a cultivation (later period) panel (W 600 mm×D 300 mm, 6 holes). Thereafter, the cultivation (later period) panel was placed in a cultivation device, and cultivation was carried out for 7 day by the DFT method (until Day 28 after seeding). The environmental conditions were controlled as described below, and light was irradiated to the plant such that the ratio of the light energy (spectral irradiance, W/m$^2$/nm) within the wavelength region of 600 nm to 700 nm to the light energy within the wavelength region of 400 nm to 800 nm was 100%.

The liquid fertilizer conditions were the same as those for the cultivation (early period) except that the electrical conductivity (EC) was 4.0 mS/cm.

<<Environmental Conditions>>

Temperature: 30° C.
Relative humidity: 60 to 80%
$CO_2$ concentration: 2000 ppm
Illumination: Average PPFD: 140 µmol/m$^2$/sec.; continuous irradiation for 24 hours; LED illumination unit "3LH series" (Nippon Medical & Chemical Instruments Co., Ltd.)

3. Infection of Plant with *Agrobacterium* and Harvest of Plant
3.1 Infection by Vacuum Infiltration The *Nicotiana benthamiana* plant on Day 28 after seeding obtained in Section 2.4 as described above was placed, in an inverted position, in the *Agrobacterium* suspension (prepared in Section 1.3 as described above) in a beaker such that all the leaves were completely immersed in the suspension.

Subsequently, the beaker was placed in a vacuum desiccator (FV-3P) (Tokyo Glass Kikai Co., Ltd.), and left to stand at a reduced pressure of 19 to 40 Torr for 1 minute. Thereafter, the valve was quickly opened to recover the pressure.

The plant was then planted, in an upright position, in a round container (round-shaped V-type container V-6) (As One Corporation) containing a liquid fertilizer (EC: 2.1 to 2.2 mS/cm, pH 5.5).

3.2 Cultivation of Infected Leaves (Expression Step)

The cultivation after infection was carried out using an artificial climate chamber (LH-410SP) (Nippon Medical & Chemical Instruments Co., Ltd.). As the light source, an LED illumination unit (3LH-256) (Nippon Medical & Chemical Instruments Co., Ltd.) was used, and the cultivation was carried out with a light/dark cycle of 16:8 hours at an average PPFD of 150 µmol/m$^2$/second. The temperature was set to 25° C. in the light period and 20° C. in the dark period during the cycles. The relative humidity was set to 60 to 85%.

3.3 Harvest of Cultivated Leaves after Infection

After 6 days of the above-described cultivation step, all the leaves, excluding the petioles, of the *Agrobacterium*-infected *Nicotiana benthamiana* plant were harvested, and stored at −80° C.

4. Measurement of GFP Expression Level
4.1 Preparation of Crude Extract

The *Agrobacterium*-infected leaves for expression of GFP and p19, preserved by freezing in Section 3.3, were placed in a mortar, and ground in liquid nitrogen. Thereafter, an extraction buffer for GFP assay (50 mM Tris-HCl, 150 mM NaCl, 2 mM EDTA, 0.1% Triton-X100 (pH7.25)) in an amount of 6 times the fresh weight of the sample was added to the leaves, and the resulting mixture was vigorously suspended to perform extraction of crude protein. To a 1.5-ml Eppendorf tube, 1 ml of the obtained crude extract was transferred, and centrifugation was carried out at 4° C. at 20,400×g for 10 minutes, followed by collection of the supernatant to be subjected to quantification of GFP as described below.

4.2 Quantification of GFP

For detection of GFP fluorescence, Wallac ARVO SX 1420 Multilabel counter (Perkin-Elmer Life Sciences) was used to detect luminescence at 507 nm that is emitted by excitation light at 485 nm. Serial dilutions of a GFP standard (rAcGFP 1 Protein, manufactured by Takara BIO Inc.) were used for the quantification. The sample was 5-fold diluted with the extraction buffer for GFP assay, and the resulting dilution was aliquoted in 100-µL volumes into wells of a 96-well microplate (Nunc FluoroNunc plate, manufactured by Thermo Fisher Scientific Inc.), followed by performing measurement to calculate the amount of GFP expressed per fresh weight (mg(kg-FW) and the amount of GFP expressed per plant (mg). The measurement results obtained from three plants were averaged, and the ratio of the obtained average to the value obtained using a three band fluorescent lamp (Comparative Example 1 below) was calculated. The obtained ratio is shown in Table 1 as a percentage.

Examples 2 to 4

Experiments were carried out in the same manner as in Example 1 except that, in the cultivation (later period) in Section 2.4, light was irradiated to the plant such that the ratio of the light energy within the wavelength region of 600 nm to 700 nm to the light energy within the wavelength region of 400 nm to 800 nm was 80% (Example 2), 60% (Example 3), or 50% (Example 4), while light within the wavelength region of 400 to 500 nm (blue light: B) was used in addition. In each condition, the measurement results obtained from three plants were averaged, and the ratio of the obtained average to the value obtained using a three band fluorescent lamp (Comparative Example 1) was calculated. The obtained ratio is shown in Table 1 as a percentage.

Comparative Example 1

An experiment was carried out in the same manner as in Example 1 except that, in the cultivation (later period) in Section 2.4, a three band fluorescent lamp "Rupika Line" (Mitsubishi Electric Corporation) was used as the illuminator. The measurement results obtained from three plants were averaged. The obtained average is shown in Table 1 as 100%.

Comparative Example 2

An experiment was carried out in the same manner as in Example 1 except that, in the cultivation (later period) in Section 2.4, light was irradiated to the plant such that the ratio of the light energy within the wavelength region of 600 nm to 700 nm to the light energy within the wavelength region of 400 nm to 800 nm was 30%, while light within the wavelength region of 400 to 500 nm (blue light: B) was used in addition. The measurement results obtained from three plants were averaged, and the ratio of the obtained average relative to the value obtained using a three band fluorescent lamp (Comparative Example 1) was calculated. The obtained ratio is shown in Table 1 as a percentage.

TABLE 1

| | Light source | Light quality during cultivation Ratio of red light 600-700 nm/ 400-800 nm energy | GFP yield (mg/Kg-FW) Ratio with respect to yield obtained with fluorescent lamp (%) |
|---|---|---|---|
| Example 1 | R | 100% | 148 |
| Example 2 | R + B | 80% | 129 |
| Example 3 | R + B | 60% | 127 |
| Example 4 | R + B | 50% | 126 |
| Comparative Example 1 | Fluorescent lamp | 23.5% | 100 |
| Comparative Example 2 | R + B | 30% | 104 |

Figure 3:
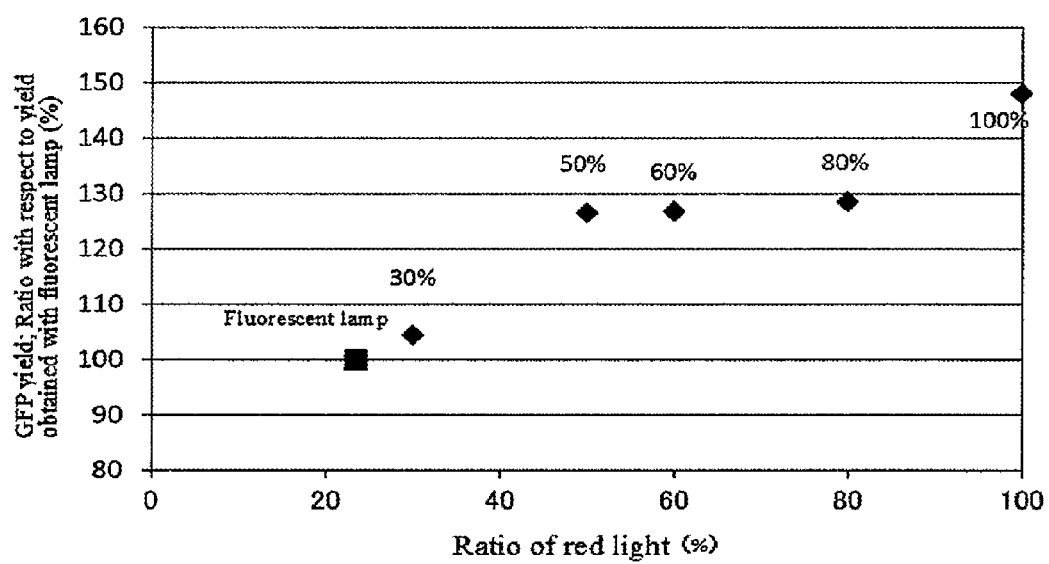
FIG. 3 is a graph illustrating the relationship between the ratio of red color and the GFP yield, wherein the result in Comparative Example 1 (fluorescent lamp) is regarded as 100%.

A graph for the GFP yield is shown in FIG. 3, and the weight of leaves upon completion of the cultivation step is shown in Table 2. As shown in Tables 1 and 2 and FIG. 3, it was found that, although the weight of leaves upon completion of the cultivation step in each Example was almost the same as that in Comparative Examples, the yield of GFP was remarkably higher in Examples, in which the ratio of light within the wavelength region of 600 nm to 700 nm (red light: R) was not less than 50%.

TABLE 2

| | Light source | Light quality during cultivation Ratio of red light 600-700 nm/ 400-800 nm energy | GFP yield (mg/Kg-FW) Ratio with respect to fluorescent lamp (%) | Leaf weight upon completion of cultivation step (g) |
|---|---|---|---|---|
| Example 1 | R | 100% | 148 | 31.3 |
| Example 3 | R + B | 60% | 127 | 31.2 |
| Comparative Example 1 | Fluorescent lamp | 23.5% | 100 | 31.3 |

[Study of Nicotine Content]

Figure 4:
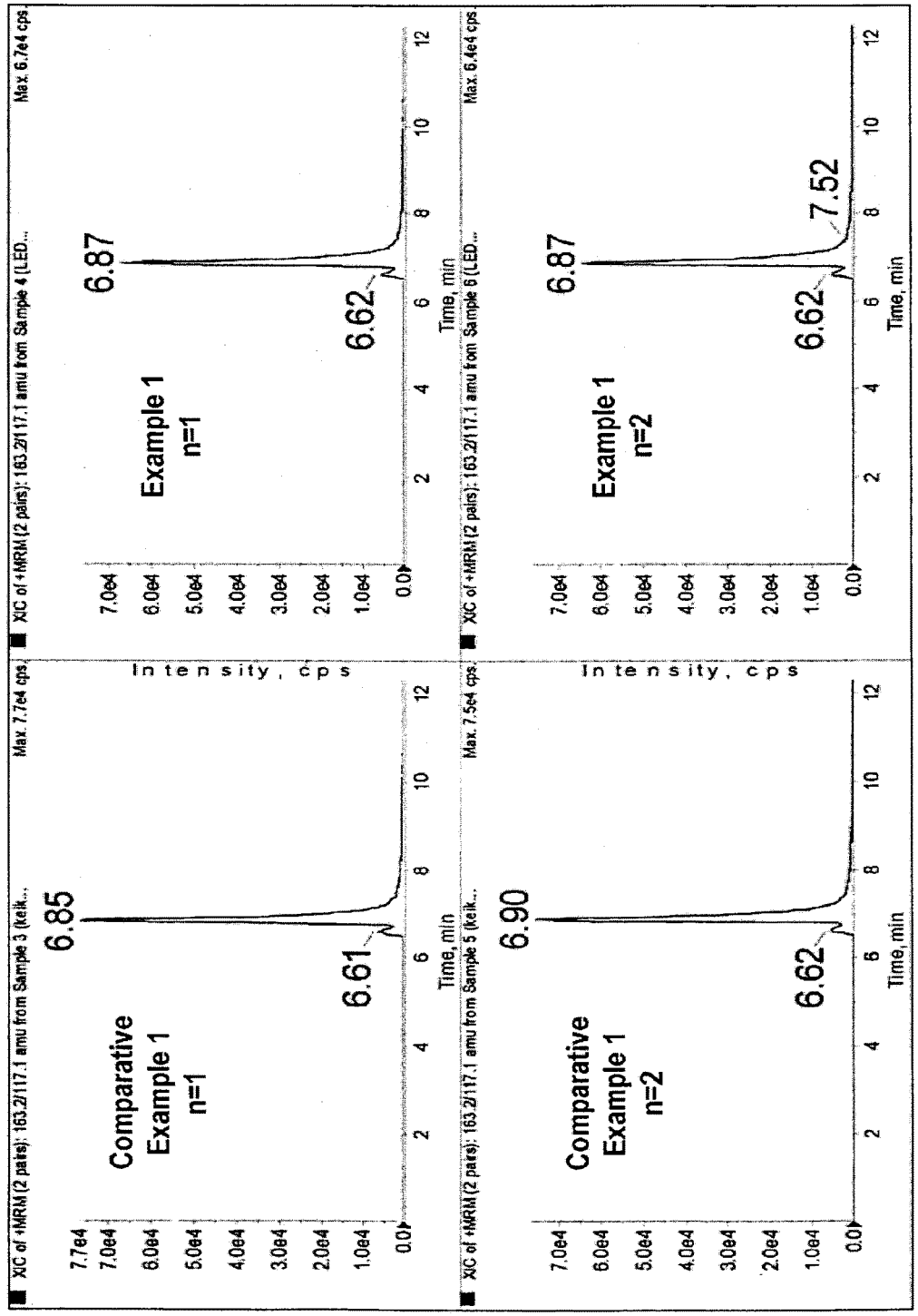
FIG. 4 illustrates the results of LC/MS analysis of the extracts (filtrates) of *Nicotiana benthamiana* cultivated in Example 1 (red light, 100%) and Comparative Example 1 (fluorescent lamp). The left column shows the results from *Nicotiana benthamiana* cultivated in Comparative Example 1 (fluorescent lamp), and the right column shows the results from *Nicotiana benthamiana* cultivated in Example 1 (red light, 100%). The top and bottom panels in each column show the results obtained by repeating the same analysis twice.

From 4.5 g of leaves of each of the *Nicotiana benthamiana* plants cultivated in Example 1 (red light, 100% R) and Comparative Example 1 (fluorescent lamp), extraction was carried out with 30 mL of acetonitrile. The resultant was 5-fold diluted with water, and the resulting dilution was subjected to ultrafiltration. Nicotine and anabasine have the same molecular formula ($C_{10}H_{14}N_2$, MW 162.12), and produce m/z 163 (=$[M+H]^+$) in electrospray ionization. Since nicotine and anabasine have similar structures, they produce the same product ions in the subsequent MS/MS analysis (m/z 163→e.g., 130, 117, 80). Therefore, nicotine and anabasine can be selectively detected by SRM (m/z 163/117). As a result of LC/MS/MS analysis (SRM, m/z 163/117) of the filtrate of the extract from tobacco leaves, two peaks corresponding to anabasine and nicotine could be detected at Minute 6.6 and Minute 6.8, respectively, as shown in FIG. 4. The intensity of the peak at Minute 6.8, which corresponds to nicotine, was 6.6 $e^4$ cps. (average of n=2) in Example 1 (FIG. 4, right column), and 7.6 $e^4$ cps. (average of n=2) in Comparative Example 1 (FIG. 4, left column). Further, it was found that the both cases show similar intensities of the peak at Minute 6.6, which corresponds to anabasine.

Thus, it was found that the nicotine content in *Nicotiana benthamiana* cultivated in Example 1 was about 10% smaller than in the case of Comparative Example 1 (fluorescent lamp).

Example 5

1. Preparation of Transformed *Agrobacterium*

1.1 Expression Plasmid

The expression was studied of a pharmaceutical protein, glucocerebrosidase (GBA1), which is a hydrolase used for a therapeutic agent for Gaucher's disease. For studying expression of GBA1, p19/MM444 used in Example 1 and the following two expression plasmids were used.

Of the p19 expression cassette (consisting of 35S promoter of cauliflower mosaic virus, the first intron of the catalase gene of castor bean, p19 gene and the terminator of the nopaline synthase gene) derived from p19/MM444, the region of the first intron of the catalase gene of castor bean and p19 gene was replaced to GBA1 gene to prepare expression plasmid for human GBA1 gene (this plasmid is hereinafter referred to as "pGBA1/MM444" (see FIG. 5 for its structure)).

The p19 gene has a function to enhance expression of the GBA1 gene, and the plasmid p19/MM444 was subjected to coexpression with pGBA1/MM444.

1.2 Transformation of *Agrobacterium* and Preparation of Glycerol Stock of Transformed *Agrobacterium*

Glycerol stocks of the transformed *Agrobacterium* were prepared according to Sections 1.2 of Example 1, except for using the above-mentioned pGBA1/MM444 instead of pGFP/MM444. The obtained transformed *Agrobacterium* strains are hereinafter referred to as GBA1-*Agrobacterium* and p19-*Agrobacterium*, respectively.

1.3 Preparation of Transformed *Agrobacterium* for Infection Step

An *Agrobacterium* suspension for the infection step (for coexpression of GBA1 and p19) was obtained according to Section 1.3 of Example 1, except for the glycerol stocks of the transformed *Agrobacterium* strains (GBA1-*Agrobacterium* and p19-*Agrobacterium*) prepared in the above Section 1.2 of Example 5 were used instead of GFP-*Agrobacterium* and p19-*Agrobacterium*.

An *Agrobacterium* suspension for the infection step (for expression of p19) was prepared according to Section 1.3 of Example 1, except that a concentrated bacterial suspension of p19-*Agrobacterium* was added to 4 L of infiltration buffer such that OD600 was 0.4 and the pH of the mixture was then adjusted to 5.6.

2. Preparation of Plant Biomass

Seeding to cultivation of *Nicotiana benthamiana* was carried out according to Sections 2.1 to 2.4 of Example 1.

3. Infection of Plant with *Agrobacterium* and Harvest of Plant

The step from infection with *Agrobacterium* to harvest of the infected leaves were carried out according to Sections 3.1 to 3.3 of Example 1, except for using each of the *Agrobacterium* suspension for the infection step (for coexpression of GBA1 and p19) and the *Agrobacterium* suspension for the infection step (for expression of p19).

4. Measurement of GBA1 Expression Level 4.1 Preparation of Crude Extract

The leaves infected with *Agrobacterium* for coexpression of GBA1 and p19, or the leaves infected with *Agrobacterium* for expression of p19, both of which were preserved by freezing in the above Section 3.3, were placed in a mortar, and ground in liquid nitrogen. Thereafter, an extraction buffer for GBA1 (20 mM Tris-HCl (pH7.2), 20 mM EDTA, 20 mM L-ascorbic acid, 0.1% Triton-X100, one tablet/50 mL complete protease inhibitor EDTA-free (Roche)) in an amount of 2 times the fresh weight of the sample was added to the leaves, and the resulting mixture was vigorously suspended to perform extraction of crude protein. To a 1.5-ml Eppendorf tube, 1 ml of the obtained crude extract was transferred, and centrifugation was carried out at 4° C. at 20,400×g for 10 minutes, followed by collection of the supernatant to be subjected to measurement of GBSI enzyme activity as described below.

The concentration of total soluble protein in these crude extract were measured by a Bradford method with protein assay available from Bio-Rad Laboratories and bovine serum albumin (BSA) as the reference protein 4.2 Measurement of GBA1 Enzyme Activity The enzyme activity of GBA1 was measured in order to confirm the level of GBA1 expression. The measurement of GBA1 enzyme activity was carried out as follows.

4 μL of the crude extract obtained in the above Section 4.1 was added to 396 μL of a reaction buffer (60 mM citrate/phosphate buffer (pH 5.5), 0.15% Triton X-100, 0.4% sodium taurocholate, 4 mM p-nitrophenyl-β-D-glucopyranoside). After mixing, the reaction was carried out at 37° C. for two hours. After the reaction, 100 μL of 0.1 M 2-amino-2-methyl-1-propanol was added to quench the reaction.

To quantitate p-nitrophenol produced by the GBA1 enzyme activity, Wallac ARVO SX 1420 Multilabel counter (Perkin-Elmer Life Sciences) was used to measure the absorbance at 405 nm. A series of serially diluted 0.2% (w/v) p-nitrophenol solution (Wako Pure Chemical Industries, Ltd.) was used as a quantitative standard.

For each sample, the amount of reaction product per gram of the total soluble protein as measured in Section 4.1 (μmol/g-TSP) was calculated. The average of the quantitation results obtained from the leaves of three plants infected with *Agrobacterium* for expression of p19 was defined as the background by the endogenous enzyme (glucosidase) in *Nicotiana benthamiana*. On the other hand, a value subtracting the above-mentioned background by the endogenous enzyme from the average of the quantitation results obtained from the leaves of four plants infected with *Agrobacterium* for coexpression of GBA1 and p19 was defined as the amount of the reaction product of GBA1. As the amount of GBA1 reaction product correlates with the level of GAB1 expression, the comparison of Examples 5 and 6 with Comparative Example 3 was conducted, assuming the amount of the reaction product as the level of GBA1 expression.

The ratio of the value relative to the value obtained using a three band fluorescent lamp (Comparative Example 3) was calculated. The obtained ratio is shown in Table 3 as a percentage.

Example 6

Experiments are carried out according to Example 5, except that, in the cultivation (later period) in Section 2.4, light was irradiated to the plant such that the ratio of the light energy within the wavelength region of 600 nm to 700 nm to the light energy within the wavelength region of 400 nm to 800 nm was 50%, while light within the wavelength region of 400 to 500 nm was used in addition in the rest of cultivation period.

The average of the quantitation results obtained from the leaves of three plants infected with *Agrobacterium* for expression of p19 was defined as the background by the endogenous enzyme (glucosidase) in *Nicotiana benthamiana*. On the other hand, a value subtracting the above-mentioned background by the endogenous enzyme from the average of the quantitation results obtained from the leaves of four plants infected with *Agrobacterium* for coexpression of GBA1 and p19 was defined as the amount of the reaction product of GBA1. As the amount of GBA1 reaction product correlates with the level of GAB1 expression, the comparison of Examples 5 and 6 with Comparative Example 3 was conducted, assuming the amount of the reaction product as the level of GBA1 expression.

The ratio of the value relative to the value obtained using a three band fluorescent lamp (Comparative Example 3) was calculated. The obtained ratio is shown in Table 3 as a percentage.

Comparative Example 3

Experiments are carried out according to Example 5, except that, in the cultivation (later period) in Section 2.4, a three band fluorescent lamp "Rupika Line" (Mitsubishi Electric Corporation) was used as the illuminator. The average of the quantitation results obtained from the leaves of three plants infected with *Agrobacterium* for expression of p19 was defined as the background by the endogenous enzyme (glucosidase) in *Nicotiana benthamiana*. On the other hand, a value subtracting the above-mentioned background by the endogenous enzyme from the average of the quantitation results obtained from the leaves of four plants infected with *Agrobacterium* for coexpression of GBA1 and p19 was defined as the amount of the reaction product of GBA1. As the amount of GBA1 reaction product correlates with the level of GAB1 expression, the comparison of Examples 5 and 6 with Comparative Example 3 was conducted, assuming the amount of the reaction product as the level of GBA1 expression. The ratio of the value relative to the value obtained using a three band fluorescent lamp (Comparative Example 3) was calculated. The obtained ratio is shown in Table 3 as a percentage.

TABLE 3

| | Light quality during cultivation | | GBA1 enzyme activity (amount of reaction product after 2 hour reaction per gram of total soluble protein (µmol/g-TSP) Ratio with respect to fluorescent lamp (%) |
|---|---|---|---|
| | Light source | Ratio of red light 600-700 nm/ 400-800 nm energy | |
| Example 5 | R | 100% | 299 |
| Example 6 | R + B | 50% | 237 |
| Comparative Example 3 | Fluorescent lamp | 23.5% | 100 |

As shown in Table 3, it was found that GBA1 yield was remarkably increased, as GBA1 expression was increased more than twice in Examples 5 and 6, where the ratio of the light within the wavelength region of 600 nm to 700 nm (red light: R) was no less than 50%, compared with Comparative Example 3, where the fluorescent light was used.

Example 7

1. Preparation of Transformed *Agrobacterium*
1.1 Expression Plasmid

For studying expression of Norwalk virus capsid protein (NVCP), p19/MM444 used in Example 1 and the following two expression plasmids were used.

Of the p19 expression cassette (consisting of 35S promoter of cauliflower mosaic virus, the first intron of the catalase gene of castor bean, p19 gene and the terminator of the nopaline synthase gene) derived from p19/MM444, the region of the first intron of the catalase gene of castor bean and p19 gene was replaced to NVCP gene to prepare expression plasmid for NVCP gene of Norwalk virus (this plasmid is hereinafter referred to as "pNVCP/MM444" (see FIG. 6 for its structure)).

The p19 gene has a function to enhance expression of the NVCP gene, and the plasmid p19/MM444 was subjected to coexpression with pNVCP/MM444.

1.2 Transformation of *Agrobacterium* and Preparation of Glycerol Stock of Transformed *Agrobacterium*

Glycerol stocks of the transformed *Agrobacterium* were prepared according to Sections 1.2 of Example 1, except for using the above-mentioned pNVCP/MM444 instead of pGFP/MM444. The obtained transformed *Agrobacterium* strains are hereinafter referred to as NVCP-*Agrobacterium* and p19-*Agrobacterium*, respectively.

1.3 Preparation of Transformed *Agrobacterium* for Infection Step

An *Agrobacterium* suspension for the infection step (for coexpression of NVCP and p19) was obtained according to Section 1.3 of Example 1, except for the glycerol stocks of the transformed *Agrobacterium* strains (NVCP-*Agrobacterium* and p19-*Agrobacterium*) prepared in the above Section 1.2 of Example 7 were used instead of GFP-*Agrobacterium* and p19-*Agrobacterium*.

2. Preparation of Plant Biomass

Seeding to cultivation of *Nicotiana benthamiana* was carried out according to Sections 2.1 to 2.4 of Example 1.

3. Infection of Plant with *Agrobacterium* and Harvest of Plant

Infection with *Agrobacterium* to harvest of the infected leaves was carried out according to Sections 3.1 to 3.3 of Example 1, except for using each of the *Agrobacterium* suspension for the infection step (for coexpression of NVCP and p19).

4. Measurement of NVCP Expression Level
4.1 Preparation of Crude Extract

The leaves infected with *Agrobacterium* for coexpression of NVCP and p19, or the leaves infected with *Agrobacterium* for expression of p19, both of which were preserved by freezing in the above Section 3.3, were placed in a mortar, and ground in liquid nitrogen. Thereafter, an extraction buffer for NVCP (25 mM Tris-HCl (pH6.6), 100 mM NaCl, 1 mM EDTA, 0.4 µg/mL sodium pyrosulfite, 0.1% Triton-X100, one tablet/50 mL complete protease inhibitor EDTA-free (Roche)) in an amount of 2 times the fresh weight of the sample was added to the leaves, and the resulting mixture was vigorously suspended to perform extraction of crude protein. To a 1.5-ml Eppendorf tube, 1 ml of the obtained crude extract was transferred, and centrifugation was carried out at 4° C. at 20,400×g for 10 minutes, followed by collection of the supernatant to be subjected to measurement of NVCP with the Western blotting technique as described below.

The concentration of total soluble protein in these crude extract were measured by a Bradford method with protein assay available from Bio-Rad Laboratories and bovine serum albumin (BSA) as the reference protein 4.2 Quantitation of NVCP NVCP was quantitatively measured with the Western blotting technique as follows.

To a twenty-fold dilution of the above-mentioned crude extract with PBS, equal volume of SDS-PAGE sample buffer (62.5 mM Tris-HCl, 2% SDS, 350 mM DTT, 25% glycerol, 0.01% BPB) was added and heat-denatured at 95° C. for 5 minutes to prepare a sample for electrophoresis. 10 µL of the sample for electrophoresis was applied to a sample well of Mini-PROTEAN TGX Gel (10%, 15-well comb, BIO-RAD) and the electrophoresis was carried out at constant voltage of 200 V for 35 minutes. The gel after the electrophoresis was stacked with Trans-Blot Turbo Transfer Pack (Mini format 0.2 µm PVDF, BIO-RAD) and assembled into Trans-Blot Turbo Transfer System (BIO-RAD). Transfer to the membrane was carried out at constant voltage of 25 V for seven minutes.

The PVDF membrane after transfer was reacted for one hour at room temperature with 1.25 µg/mL of mouse monoclonal antibody against norovirus GL1 (P2B2, Ahearn). After rinsing with TBS-T, the membrane was further reacted for one hour at room temperature with 0.13 µg/mL of AP conjugated antibody against mouse IgG (H+L) (Promega). Detection was carried out with Western Lightning CDP-Star Chemiluminescence Reagent (Perkin-Elmer). Imaging and quantitative analysis of the signal was carried out with ImageQuant LAS500 and ImageQuant TL software (GE Healthcare), respectively.

For each sample, a relative value of NVCP per gram of total soluble protein as measured in Section 4.1 was calculated. The ratio of average of the quantitation results obtained from the leaves of four plants relative to the value obtained using a three band fluorescent lamp (Comparative Example 4) was calculated. The obtained ratio is shown in Table 4 as a percentage.

Example 8

Experiments are carried out according to Example 7, except that, in the cultivation (later period) in Section 2.4, light was irradiated to the plant such that the ratio of the light energy within the wavelength region of 600 nm to 700 nm to the light energy within the wavelength region of 400 nm to 800 nm was 50%, while light within the wavelength region of 400 to 500 nm was used in addition in the rest of cultivation period.

The ratio of average of the quantitation results obtained from the leaves of four plants relative to the value obtained using a three band fluorescent lamp (Comparative Example 4) was calculated. The obtained ratio is shown in Table 4 as a percentage.

Comparative Example 4

Experiments are carried out according to Example 5, except that, in the cultivation (later period) in Section 2.4, a three band fluorescent lamp "Rupika Line" (Mitsubishi Electric Corporation) was used as the illuminator.

The average of the quantitation results obtained from the leaves of four plants was used to normalize the average values obtained in Examples 7 and 8 as a percentage in Table 4.

TABLE 4

| | Light quality during cultivation | | NVCP yield (amount of reaction product after 2 hour reaction per gram of total soluble protein (µmol/g-TSP) Ratio with respect to fluorescent lamp (%) |
|---|---|---|---|
| | Light source | Ratio of red light 600-700 nm/ 400-800 nm energy | |
| Example 7 | R | 100% | 170 |
| Example 8 | R + B | 50% | 123 |
| Comparative Example 4 | Fluorescent lamp | 23.5% | 100 |

As shown in Table 4, it was found that the NVCP yield was remarkably increased, as NVCP expression was increased 1.2- to 1.7-fold in Examples 7 and 8, where the ratio of the light within the wavelength region of 600 nm to 700 nm (red light: R) was no less than 50%, compared with Comparative Example 4, where the fluorescent light was used.

Reference Examples 1, 2

Experiments are carried out to prepare the plant biomass according to Example 1, except that, in the cultivation (later period) in Section 2.4, light was irradiated to the plant such that PPFD of the illumination (LED lighting unit "3LH series") was set at 40 µmol/m²/sec and the ratio of the light energy within the wavelength region of 400 nm to 500 nm to the light energy (spectral irradiance, W/m²/nm) within the wavelength region of 400 nm to 800 nm was 42%, the ratio of the light energy within the wavelength region of 501 nm to 600 nm was 20%, the ratio of the light energy within the wavelength region of 601 nm to 700 nm was 38% and far-infrared light (FR) of 701 nm to 800 nm was additionally irradiated. The ratio (FR/R) of light energy of far-infra red light (FR, 701 to 800 nm) to red light (R, 601 to 700 nm) in Reference Examples 1 and 2 were set at 1 and 2, respectively. The distance from the upper face of the urethane to the shoot apex was measured as plant height (cm).

As for other steps, experiments were carried out according to Example 1.

The ratio of average of the quantitation results obtained from the leaves of four plants relative to the value obtained using a three band fluorescent lamp (Comparative Example 5) was calculated. The obtained height and ratio of GFP are shown in Table 5 as a percentage.

Comparative Example 5

Experiments are carried out according to Reference Examples, except that, in the cultivation (later period) in Section 2.4, a three band fluorescent lamp "Rupika Line" (Mitsubishi Electric Corporation) was used as the illuminator. The average of the quantitation results obtained from the leaves of four plants was used to normalize the average values for GFP yield obtained in Reference Examples 1 and 2 as a percentage in Table 5.

TABLE 5

| | Light quality during cultivation | | Plant height cm | GFP yield (mg/Kg-FW) Ratio with respect to yield obtained with fluorescent lamp (%) |
|---|---|---|---|---|
| | Light source | FR/R | | |
| Reference Example 1 | R + G + B | 1 | 15.8 | 107 |
| Reference Example 2 | R + G + B | 0 | 5.9 | 104 |
| Comparative Example 5 | Fluorescent lamp | 0.1 | 6.1 | 100 |

As shown in Table 5, it was found that the plant height had a tendency to become taller with irradiation in the cultivation step of far-infra red light (FR, wavelength 701 to 800 nm). In Reference Example 1 where FR/R is one or more, the plant height became remarkably taller and the ratio of leaves in the entire aerial part is lower. It is considered that the condition reduces the yield of leaves and the purification load as the ratio of stalk increases. It was found that the condition is unfitted to the cultivation in a multi-level cultivation plant factory.

The invention claimed is:

1. A method for producing a protein in a plant, the method comprising:
    cultivating the plant;
    infecting the cultivated plant with *Agrobacterium* having a polynucleotide encoding the protein; and
    allowing the infected plant to express the protein;
    wherein the plant is exposed during a late period of the cultivating the plant and not during the infecting and when the infected plant expresses the protein to lighting conditions where the ratio of light energy within the wavelength region of 600 nm to 700 nm to light energy within the wavelength region of 400 nm to 800 nm is not less than 50%.

2. The method according to claim 1, wherein the ratio is not less than 75%.

3. The method according to claim 1, further comprising purifying and collecting the expressed protein.

4. The method according to claim 1, wherein the protein is a pharmaceutical protein.

5. The method according to claim 1, wherein the plant is a tobacco plant.

6. The method according to claim 1, wherein the plant is cultivated in a closed plant factory.

7. The method according to claim 1, wherein a light emitting diode (LED) is used as a light energy source in the cultivating.

8. The method according to claim 1, wherein the protein is an enzyme or a virus-like particle.

9. The method according to claim 1, wherein the ratio is not less than 90%.

10. The method according to claim 1, wherein at least a part of the cultivating is carried out under lighting conditions where the ratio (FR/R) of the light energy within the wavelength region of 601 nm to 700 nm (R) to the light energy within the wavelength region of 701 nm to 800 nm (FR) is not more than 0.25.

11. The method according to claim 1, wherein the cultivating is hydroponic cultivating.

12. The method according to claim 1, wherein the plant is a tobacco plant and wherein the height of the plant in the cultivating is from 2 cm to 25 cm.

13. The method according to claim 1, wherein the plant is a tobacco plant and wherein the aerial part fresh weight of the plant in the cultivating is from 3 g to 100 g.

14. The method according to claim 1, wherein the plant is a tobacco plant and wherein the leaf weight of the plant in the cultivating is from 2.5 g to 80 g.

15. The method according to claim 1, wherein at least a part of the cultivating comprises a carbon dioxide concentration of 500 ppm to 3000 ppm.

16. The method according to claim 1, wherein at least a part of the cultivating is carried out under temperature of from 10° C. to 40° C.

17. The method according to claim 1, wherein at least a part of the cultivating is carried out under humidity of from 40% to 95%.

18. The method according to claim 1, wherein the cultivating is performed on a plant cultivation container shelf that is in the form of a multi-level shelf.

19. The method according to claim 1, further comprising raising a seedling before the cultivating.

* * * * *